United States Patent [19]
Mayahara et al.

[11] Patent Number: 6,159,928
[45] Date of Patent: Dec. 12, 2000

[54] CIS-CONFIGURATIONAL UNSATURATED ESTER, PROCESS FOR PRODUCING THE SAME, AND FRAGRANCE COMPOSITION CONTAINING THE SAME

[75] Inventors: Kunio Mayahara; Toshiki Mori; Yoshin Tamai, all of Niigata, Japan

[73] Assignee: Kuraray Co., Ltd., Kurashiki, Japan

[21] Appl. No.: 09/289,395

[22] Filed: Apr. 12, 1999

[30] Foreign Application Priority Data

Apr. 13, 1998 [JP] Japan .................................. 10-117872
Dec. 4, 1998 [JP] Japan .................................. 10-345670

[51] Int. Cl.$^7$ ............................ A61K 7/46; C07C 69/00; C07C 69/52
[52] U.S. Cl. ............................ 512/26; 560/129; 560/205
[58] Field of Search .................................. 560/129, 205; 512/26

[56] References Cited

U.S. PATENT DOCUMENTS 4,387,047  6/1983  Sundt et al. ........................ 252/522 R
5,405,974  4/1995  Murahashi et al. ..................... 549/266
5,652,205  7/1997  Hartman et al. ........................ 510/101

OTHER PUBLICATIONS

Steffen Arctander, Perfume and Flavor Chemicals II, 1 page, "2159: Methyl Pentenyl Acetate", 1969.

Ernest Wenkert, et al., J. Org. Chem., vol. 49, No. 25, pp. 4894–4899, "Transformation of Carbon–Oxygen into Carbon–Carbon Bonds Mediated by Low–Valent Nickel Species", 1984.

Ernest Wenkert, et al., Journal of the American Chemical Society, vol. 101, No. 8, pp. 2246–2247, "Nickel–Induced Conversion of Carbon–Oxygen into Carbon–Carbon Bonds. One–Step Transformations of Enol Ethers Into Olefins and Aryl Ethers into Biaryls", Apr. 11, 1979.

Jean–Philippe Ducoux, et al., Tetrahedron, vol. 48, No. 31, pp. 6403–6412, "An Efficient and Stereoselective Synthesis of Insect Pheromones by Way of Nickel–Catalyzed Grignard Reactions[1]. Syntheses of Gossyplure and Pheromones of Eudia Pavonia and Drosophila Melanogaster.", 1992.

Allen B. Reitz, et al., J. Org. Chem. vol. 52, No. 19, pp. 4191–4202, "Stereoselectivity of Electrophile–Promoted Cyclizations of γ–Hydroxyalkenes. An Investigation of Carbohydrate–Derived and Model Substrates", 1987.

Waldemar Adam, , et al., J. Am. Chem. Soc., vol. 118, No. 8, pp. 1899–1905, "Diastereoselective Singlet Oxygen Ene Reaction (Schenck Reaction) and Diastereoselective Epoxidations of Heteroatom–Substituted Acyclic Chiral Olefins: A Mechanistic Comparison", 1996.

Edward D. Mihelich, et al., J. Am. Chem. Soc., vol. 103, No. 25, pp. 7690–7692, "Vanadium–Catalyzed Epoxidations. 2. Highly Stereoselective Epoxidations of Acyclic Homoallylic Alcohols Predicted by a Detailed Transition–State Model[1]", 1981.

Kohei Tamao, et al., J. Am. Chem. Soc., vol. 108, No. 19, pp. 6090–6093, "Stereocontrol in Intramolecular Hydrosilation of Allyl and Homoallyl Alcohols: A New Approach to the Stereoselective Synthesis of 1,3–Diol Skeletons[1]", 1986.

Denis Prat, et al., Tetrahedron Letters, vol. 27, No. 6, pp. 711–714, "Stereoselective Epoxidation of Allylic and Homoallylic Alcohols with 30% Hydrogen Peroxide Catalyzed by Tungstic Acid in Buffered Media", 1986.

Claudio Fuganti, et al., J. C. S. Chem. Comm., pp. 995–997, "Efficient Stereoselective Synthesis of Natural α–Tocopherol (Vitamin E)", 1979.

Primary Examiner—Jill Warden
Assistant Examiner—Monique T. Cole
Attorney, Agent, or Firm—Oblon, Spivak, McClelland, Maier & Neustadt, P.C.

[57] ABSTRACT

The present invention provides a cis-configurational unsaturated ester represented by the formula (1)

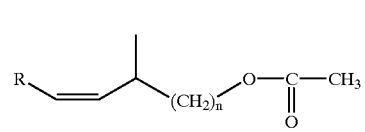

(1)

(where R is a methyl group or a phenyl group, and n is 1 or 2)

and also provides a fragrance composition containing the cis-configurational unsaturated ester in an effective amount. The cis-configurational unsaturated ester represented by the formula (1) can be produced by reacting a cyclic vinyl ether represented by the formula (2a)

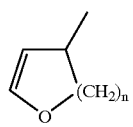

(2a)

(where n is defined as above) with a Grignard reagent represented by the formula (3a)

RMgX  (3a)

(where R is defined as above, and X is a chlorine atom, a bromine atom or an iodine atom)

in the presence of a triarylphosphine and not more than 0.05 mol of a nickel compound per one mole of the cyclic vinyl ether represented by the formula (2a) to give a cis-configurational unsaturated alcohol represented by the formula (4a)

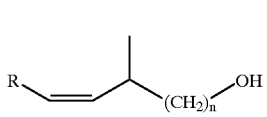

(4a)

(where n and R are defined as above); and subjecting this cis-configurational unsaturated alcohol to acylation with acetic acid or a derivative thereof to give the cis-configurational unsaturated esters represented by the formula (1).

6 Claims, No Drawings

CIS-CONFIGURATIONAL UNSATURATED ESTER, PROCESS FOR PRODUCING THE SAME, AND FRAGRANCE COMPOSITION CONTAINING THE SAME

BACKGROUND OF THE INVENTION

1. Field of the Invention

The present invention relates to a cis-configurational unsaturated ester having a unique odor. The present invention also relates to a fragrance composition containing this cis-configurational unsaturated ester.

2. Description of the Related Art 3-hexenyl acetate (having a Japanese radish-like odor), 3-isopropyl-5-hepten-3-yl acetate (having a floral note), 4,8-dimethyl-7-nonen-4-yl acetate (having a lemony note) and the like were known as unsaturated esters used for perfumery. Other known chemicals used for perfumery are unsaturated alcohols, such as 3-hexen-1-ol (also known as leaf alcohol, having a green note), 2-methyl-3-hexen-2-ol (having a parsley-like odor), 1-octen-3-ol (also known as Matsutake alcohol), 2,4-dimethyl-2-hexen-4-ol (having a mint or camphor-like odor) (Osamu Okuda, "Koryo Kagaku Soran 2," p. 502 to p. 508 and p. 1289 to p. 1293, published by Hirokawa Publishing Co.).

Thus, some unsaturated esters and unsaturated alcohols have a unique odor, and these are widely used for perfumery. These compounds each have their own characteristic odor hat is caused by their difference in the number of carbons in their main chain of the basic carbon skeleton, whether they are branched or not, the structure of the carbon—carbon double bonds.

There has long been a great need to give various changes to the odor of perfume preparations. Therefore, there is a great need for novel compounds that have a structure of unsaturated esters or alcohols and have a unique odor different from those of conventional unsaturated esters or alcohols, and that can allow the odor of other fragrance components to be varied or enhanced.

SUMMARY OF THE INVENTION

An object of the present invention is to provide a novel compound that satisfies the above need, a process for producing this compound, and a fragrance composition containing this compound.

Specifically, the present invention provides a cis-configurational unsaturated ester represented by the formula (1)

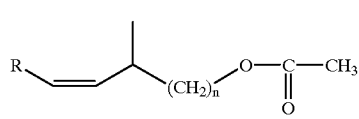

(1)

(where R is a methyl group or a phenyl group, and n is 1 or 2)
and also provides a fragrance composition containing the cis-configurational unsaturated ester in an effective amount.

The present invention also provides a process for producing the cis-configurational unsaturated ester represented by the formula (1), comprising the steps of:
reacting a cyclic vinyl ether represented by the formula (2a)

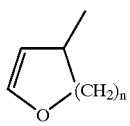

(2a)

(where n is defined as above)
with a Grignard reagent represented by the formula (3a)

(where R is defined as above, and X is a chlorine atom, a bromine atom, or an iodine atom)
in the presence of a triarylphosphine and not more than 0.05 mol of a nickel compound per one mole of the cyclic vinyl ether represented by the formula (2a) to give a cis-configurational unsaturated alcohol represented by the formula (4a)

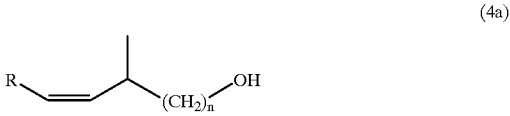

(4a)

(where n and R are defined as above); and
subjecting this cis-configurational unsaturated alcohol to acylation with acetic acid or a derivative thereof to give the cis-configurational unsaturated esters represented by the formula (1).

The present invention also provides a process for producing the cis-configurational unsaturated alcohol represented by the formula (4) including the cis-configurational unsaturated alcohol represented by the formula (4a)

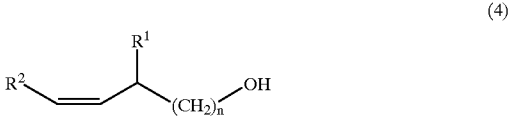

(4)

(where $R^1$ is a hydrogen atom or a methyl group, $R^2$ is an alkyl group with a carbon number of 10 or less, an alkenyl group with a carbon number of 10 or less, an aralkyl group with a carbon number of 10 or less or an aryl group with a carbon number of 10 or less, and n is 1 or 2) comprising the step of:
reacting a cyclic vinyl ether represented by the formula (2)

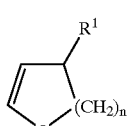

(2)

(where n and R are defined as above)
with a Grignard reagent represented by the formula (3)

(where $R^2$ and X are defined as above)
in the presence of a triarylphosphine and not more than 0.05 mol of a nickel compound per one mole of the cyclic vinyl ether represented by the formula (2) to give the cis-configurational unsaturated alcohol represented by the formula (4).

This and other objects, features and advantages of the present invention are described in or will become apparent from the following detailed description of the invention.

DETAILED DESCRIPTION OF THE INVENTION

Preferred examples of the cis-configurational unsaturated ester represented by the formula (1) include 2-methyl-cis-3-pentenyl acetate (in the formula (1), n=1 and R=Me); 3-methyl-cis-4-hexenyl acetate (in the formula (1), n=2 and R=Me); 2-methyl-4-phenyl-cis-3-butenyl acetate (in the formula (1), n=1 and R=Ph); and 3-methyl-5-phenyl-cis-4-pentenyl acetate (in the formula (1), n=2 and R=Ph), where the term "Me" is a methyl group and the term "Ph" is a phenyl group.

The above-mentioned cis-configurational unsaturated ester of the present invention has a unique odor and is a useful compound for perfumery. In particular, 3-methyl-cis-4-hexenyl acetate has a fruity note, such as the odor of pears or apples, with a green note.

The fragrance composition of the present invention containing an effective amount of the cis-configurational unsaturated ester of the formula (1) can be used in a various applications, for examples, perfumes; air fresheners; toiletries such as soap, lotions, cosmetic cream, pomade, hair tonics, shampoos and hair rinses; bath salts; cleansers and cleaners. The fragrance composition can also be used to give a fragrance to foods, fibers, sheets, cloth, paper, paint, ink, clay, woods, furniture, carpets, sanitary goods, erasers, man-made leather, plastics and the like.

The effective amount of the cis-configurational unsaturated ester of the formula (1) in the fragrance composition of the present invention is usually 0.01% by weight or more, preferably 0.1 to 95% by weight, and more preferably 1 to 40% by weight, on the basis of the total weight of the fragrance composition.

In addition to the cis-configurational unsaturated ester of the formula (1), the fragrance composition of the present invention can also contain water; alcohols such as ethanol, 2-propanol, benzyl alcohol, phenethyl alcohol, 3-methyl-3-methoxybutanol, linalool, tetrahydrolinalool, citronellol, glycerol and 1,3-butanediol; ketones such as α-ionone and irone; aldehydes such as citral and citronellal; esters such as ethyl acetate, benzyl acetate and benzyl salicylate; hydrocarbons such as squalane; carboxylic acids such as stearic acid and oleic acid; sugars such as cyclodextrin; vaseline, microcrystalline wax and the like.

The fragrance composition of the present invention can also contain thickeners such as carboxymethyl cellulose, casein, sodium polyacrylate and polyvinyl alcohol; antiseptics; UV absorbents; antioxidants; surfactants; pigments; inorganic fillers such as silica, alumina and talc; and the like.

The fragrance composition of the present invention can be prepared by mixing the cis-configurational unsaturated ester represented by the formula (1) with other components by conventional methods.

Next, the process for producing the cis-configurational unsaturated ester represented by the formula (1) will be described. This process comprises the steps of allowing the cyclic vinyl ether of the formula (2a) to react with the Grignard reagent of the formula (3a) to give the unsaturated alcohol of the formula (4a), and then subjecting this unsaturated alcohol to acylation with acetic acid or a derivative thereof.

The following description will also deal with a novel process for producing the unsaturated alcohol of the formula (4) including the unsaturated alcohol of the formula (4a), characterized in that the cyclic vinyl ether of the formula (2) including the cyclic vinyl ether of the formula (2a) is allowed to react with the Grignard reagent of the formula (3) including the Grignard reagent of the formula (3a). Here, the cyclic vinyl ether of the formula (2a) is the compound in which $R^1$ in the formula (2) is a methyl group, the Grignard reagent of the formula (3a) is the compound in which $R^2$ in the formula (3) is a methyl group or a phenyl group, and the unsaturated alcohol of the formula (4a) is the compound in which $R^1$ in the formula (4) is a methyl group and $R^2$ is a methyl group or a phenyl group.

The cyclic vinyl ether represented by the formula (2), which is used as a starting material, is 2,3-dihydrofuran (n=1, $R^1$=a hydrogen atom), 3-methyl-2,3-dihydrofuran (n=1, $R^1$=a methyl group), 3,4-dihydro-2H-pyran (n=2, $R^1$=a hydrogen atom), or 4-methyl-3,4-dihydro-2H-pyran (n=2, $R^1$=a methyl group). As the cyclic vinyl ether, a commercially available product may be used, or one prepared by the process disclosed in Japanese Patent Application Laid-Open No. 3-26177 may be used.

The cyclic vinyl ether of the formula (2a) is, among the compounds listed above, 3-methyl-2,3-dihydrofuran (n=1) or 4-methyl-3,4-dihydro-2H-pyran (n=2).

The cyclic vinyl ether represented by the formula (2) or the formula (2a) is usually used in an amount of 0.8 to 5 mol, preferably 0.8 to 1 mol per one mole of the Grignard reagent represented by the formula (3) or the formula (3a).

In the formula (3), examples of the alkyl group with a carbon number of 10 or less represented by $R^2$ include a methyl group, an ethyl group, a propyl group, isopropyl group, a n-butyl group, a t-butyl group, a n-hexyl group, a 2-ethylhexyl group and a n-octyl group; and examples of the alkenyl group with a carbon number of 10 or less include a vinyl group, a 2-propenyl group, a 1-propenyl group, a 1-butenyl group, a 2-butenyl group, a 3-methyl-2-butenyl group and a 1-octenyl group. Examples of the aralkyl group with a carbon number of 10 or less represented by $R^2$ include a benzyl group and a phenethyl group, and examples of the aryl group with a carbon number of 10 or less include a phenyl group and a tolyl group. Of these, a methyl group or a phenyl group is preferable as $R^2$.

The Grignard reagent of the formula (3a) corresponds to a favorable embodiment of the Grignard reagent of the formula (3). Specifically, the Grignard reagent of the formula (3a) is the compound in which $R^2$ in the formula (3) is a methyl group or a phenyl group.

The Grignard reagent represented by the formula (3) or the formula (3a) is commercially available as a solution of diethyl ether or tetrahydrofuran, or can be prepared by the reaction of metallic magnesium with a compound represented by the formula $R^2X$ or RX (where $R^2$, R and X are defined as above) in diethyl ether or tetrahydrofuran according to the method described in the literature (eg, Shin Jikken Kagaku Koza, Vol. 12, Yuki Kinzoku Kagaku, p. 62).

From the point of reaction rate, it is preferable to remove the above-mentioned diethyl ether or tetrahydrofuran as much as possible prior to the reaction of the Grignard reagent represented by the formula (3) or the formula (3a) with the cyclic vinyl ether represented by the formula (2) or the formula (2a). The diethyl ether or tetrahydrofuran can be removed by known methods such as evaporation under reduced pressure or replacement with an appropriate solvent.

Examples of the nickel compound used in the present invention include nickel(II) chloride, nickel(II) bromide, nickel(II) acetate tetrahydrate, nickel(II) acetylacetonate dihydrate, dichlorobis (triphenylphosphine) nickel(II), bis(1,5-cyclooctadiene) nickel(0), tetrakis(triphenylphosphine) nickel(0). Of these, a nickel complex having a ligand such as triphenylphosphine is preferable.

The nickel compound is used in an amount of usually 0.05 mol or less, preferably 0.00001 to 0.05 mol per one mole of the cyclic vinyl ether represented by the formula (2) or the formula (2a). From the point of higher selectivity to the cis-configurational unsaturated alcohol represented by the formula (4) or the formula (4a), it is preferable to use the nickel compound in a smaller amount, with a range of 0.00001 to 0.02 mol, more preferably 0.0001 to 0.01 mol per one mole of the cyclic vinyl ether represented by the formula (2) or the formula (2a). This range is markedly lower than the amount used in a conventional process for producing an unsaturated alcohol (approximately 0.1 mol per one mole of cyclic vinyl ether; for the reference, see J. Org. Chem., 49, 4894(1984)). Therefore, the process for producing the cis-configurational unsaturated alcohol represented by the formula (4) or the formula (4a) by the present invention is an industrially advantageous approach in terms of production cost.

Examples of the triarylphosphine used in the present invention include triphenylphosphine, tris(p-tolyl)phosphine and tris(2,4-dimethylphenyl)phosphine. Of these, triphenylphosphine is preferred for industrial applications because of its low cost.

The triarylphosphine is used in an amount of usually 0.1 to 3000 mol per one mole of nickel atoms of the above-mentioned nickel compound. From the point of reaction rate and higher selectivity to the cis-configurational unsaturated alcohol represented by the formula (4) or the formula (4a), it is preferable to use the triarylphosphine in a larger amount, with a range of 2 to 2000 mol per one mole of nickel atoms in the above-mentioned nickel compound.

The triarylphosphine may be incorporated as a ligand into the nickel compound during the reaction, depending on the type of nickel compound. In this case, the amount of the triarylphosphine should be increased, according to the amount that will be incorporated as a ligand.

The reaction of the Grignard reagent represented by the formula (3) or the formula (3a) with the cyclic vinyl ether represented by the formula (2) or the formula (2a) (hereinafter referred to as the Grignard reaction in the present invention) is usually carried out in the presence of a solvent which does not inhibit the reaction. Examples of the solvents include aromatic hydrocarbons such as benzene, toluene, xylene and mesitylene; and ethers with a low coordination property with respect to nickel, such as t-butyl methyl ether. There are no particular limitations on the amount of the solvent. The solvent can be used to the extent that do not suppress the reaction.

With the Grignard reaction in the present invention, the cyclic vinyl ether represented by the formula (2) or the formula (2a) can be used in an excessive amount in place of the above-mentioned solvent.

The Grignard reaction in the present invention is usually carried out at a temperature of 30 to 100° C., preferably 50 to 90° C. The reaction time is usually 30 minutes to 10 hours.

It is preferable to carry out the Grignard reaction in the present invention under an inert gas atmosphere such as nitrogen or argon.

Upon completion of the reaction, the cis-configurational unsaturated alcohol represented by the formula (4) or the formula (4a), the product, is separated by a conventional method, examples of which include a method that comprises the steps of pouring the reaction mixture into an aqueous ammonium chloride, dilute hydrochloric acid or the like, obtaining an organic layer containing the product by the separation of the organic layer, or by the extraction with hydrocarbons such as n-hexane, benzene or toluene; ethers such as diethyl ether; esters such as ethyl acetate; halogenated hydrocarbons such as dichloromethane, and removing the organic solvent from the obtained organic layer.

The cis-configurational unsaturated alcohol represented by the formula (4) or the formula (4a) obtained in this manner can be further purified by a known method such as distillation or column chromatography as needed.

The cis-configurational unsaturated alcohols represented by the formula (4) or the formula (4a) can be used for perfumery. Of these, the cis-configurational unsaturated alcohol represented by the formula (4a) can be converted into the cis-configurational unsaturated ester represented by the formula (1), which has a unique odor and is extremely useful for perfumery, by acylation with acetic acid or a derivative thereof such as acetic anhydrite or acetyl chloride.

Of the cis-configurational unsaturated alcohols represented by the formula (4a), 3-methyl-5-phenyl-cis-4-penten-1-ol and 2-methyl-4-phenyl-cis-3-buten-1-ol are novel compounds.

The acylation of the cis-configurational unsaturated alcohol represented by the formula (4a) with acetic acid or a derivative thereof can be carried out by a conventional esterification method disclosed in the literature (eg, Shin Jikken Kagaku Koza, Vol. 22, Yuki Gosei 4, p. 43), examples of which include (1) a method in which the cis-configurational unsaturated alcohol represented by the formula (4a) is allowed to react with 0.9 to 2 mol of acetic anhydride per one mole of the unsaturated alcohol at 0 to 50° C. and in the presence of a basic substance such as triethylamine, pyridine or sodium acetate, (2) a method in which the cis-configurational unsaturated alcohol represented by the formula (4a) is allowed to react with 0.9 to 1.5 mol of acetyl halide per one mole of the unsaturated alcohol at 0 to 50° C., in a solvent such as ether, and in the presence of a basic substance such as sodium hydroxide, pyridine or triethylamine, and (3) a method in which the cis-configurational unsaturated alcohol represented by the formula (4a) is allowed to react with 0.2 to 2 mol of acetic acid per one mole of the unsaturated alcohol in the presence of an acidic catalyst, for example, a mineral acid such as sulfuric acid, an organic acid such as paratoluenesulfonic acid, a Lewis acid such as boron trifluoride etherate.

The cis-configurational unsaturated ester represented by the formula (1), the product, can be separated by a conventional method, examples of which include i) a method that comprises the steps of pouring the reaction mixture into an aqueous ammonium chloride, dilute hydrochloric acid or the like, obtaining an organic layer containing the product by the extraction with hydrocarbons such as n-hexane, benzene, toluene; ethers such as diethyl ether; esters such as ethyl acetate; halogenated hydrocarbons such as dichloromethane, and removing the organic solvent from the obtained organic layer, or ii) a method in which the reaction mixture is separated by chromatography.

The cis-configurational unsaturated ester represented by the formula (1) obtained in this manner can be further purified by a known method such as distillation or column chromatography as needed.

EXAMPLES

The present invention will now be described in detail through examples, but the present invention is not limited to these examples.

Example 1 (Production of 3-methyl-cis-4-hexenyl acetate)

(a) Production of 3-methyl-cis-4-hexen-1-ol

A three-neck flask with a volume of 2 liters was charged with 2.88 g (4.4 mmol) of dichlorobis(triphenylphosphine)nickel(II), 2.31 g (8.8 mmol) of triphenylphosphine and 1 liter of toluene under nitrogen. 400 mL of a solution of methyl magnesium bromide in diethyl ether (concentration: 2.2 mol/liter, containing 0.88 mol of methyl magnesium bromide) was added to the resulting mixture at room temperature, followed by stirring for 15 minutes.

Thereafter, approximately 400 mL of diethyl ether was distilled off from the resulting mixture at a temperature of 25° C. or lower and a pressure of approximately 1 Torr, and 200 mL of toluene was then added to the residue. 82.6. (0.84 mol) of 4-methyl-3,4-dihydro-2H-pyran was added dopwise to the obtained mixture over 5 minutes at 20° C. under nitrogen. The temperature of the reaction mixture was raised to 50° C., followed by stirring for 4 hours at 50° C. and further stirring for 6 hours at 70° C.

The reaction mixture was cooled to room temperature, and poured into 4 liters of a saturated aqueous ammonium chloride, followed by stirring. Then the mixture was allowed to stand and separate into an organic layer and an aqueous layer. The organic layer was collected, while the aqueous layer was twice extracted with 200 mL of toluene. The organic layer and the toluene extracts were combined and analyzed by gas chromatography to find that the combined organic layer and toluene extracts contains 90.97 g (0.8 mol; yield: 95.2%) of 3-methyl-cis-4-hexen-1-ol and 0.78 g (7 mmol; yield: 0.8%) of 3-methyl-trans-4-hexen-1-ol (cis/trans=99.1/0.9).

Conditions for Gas Chromatography Analysis

Column: PEG-HT (trade name, available from Gaskuro Kogyou Inc., length: 4 m)

Column temperature: The temperature was kept at 80° C. for 8 minutes, then raised to 230° C. at a rate of 5° C./minute.

Injection temperature: 230° C.

Detector: FID detector

Carrier gas: nitrogen

The combined organic layer and the toluene extracts was distilled under reduced pressure to give 82.04 g of 3-methyl-cis-4-hexen-1-ol (boiling point: 62° C./9 Torr, purity: 98.5%).

(b) Production of 3-methyl-cis-4-hexenyl acetate

A three-neck flask with a volume of 200 mL was charged with 30.0 g (0.263 mol) of the 3-methyl-cis-4-hexen-1-ol obtained in (a) above and 1.61 g (13.2 mmol) of 4-dimethylaminopyridine. Then 53.65 g (0.526 mol) of acetic anhydride was added dropwise to the obtained mixture at a rate such that the reaction temperature did not exceed 40° C. 30 mL of n-hexane and 50 mL of water were added to the reaction mixture, followed by stirring. The resulting mixture was allowed to stand and separate into an organic layer and an aqueous layer.

The organic layer was collected, washed four times with 50 mL of water and dried over 10 g of sodium sulfate with stirring for 30 minutes. Sodium sulfate was filtered off from the mixture, and the filtrate was analyzed by gas chromatography under the analysis conditions given above to find that the filtrate contains 40.30 g (0.257 mol, yield: 97.7%) of 3-methyl-cis-4-hexenyl acetate.

The filtrate obtained above was distilled under reduced pressure to give 26.49 g of 3-methyl-cis-4-hexenyl acetate (boiling point: 84° C./25 Torr, purity: 99.4%) having a fruity and green note. The properties of this compound are shown below.

$^1$H-NMR (300 MHz, CDCl$_3$, TMS)

δ (ppm): 0.98 (d, 3H), 1.41–1.53 (m, 1H), 1.60 (q, 3H), 1.63–1.75 (m, 1H), 2.05 (s, 3H), 2.57–2.67 (m, 1H), 3.94–4.11 (m, 2H), 5.08–5.17 (m, 1H), 5.38–5.48 (m, 1H)

$^{13}$C-NMR (300 MHz, CDCl$_3$, TMS)

δ (ppm): 13.01, 21.14, 21.24, 28.24, 36.02, 63.20, 123.59, 135.70, 171.29

Example 2 (Production of 2-methyl-cis-3-pentenyl acetate)

(a) Production of 2-methyl-cis-3-penten-1-ol

A Grignard reaction was conducted by the same manner in Example 1 (a) except that 43.1 g (0.512 mol) of 3-methyl-2,3-dihydrofuran was used instead of the 4-methyl-3,4-dihydro-2H-pyran.

The reaction mixture was cooled to room temperature, and poured into 2 liters of a saturated aqueous ammonium chloride, followed by stirring. Then the mixture was allowed to stand and separate into an organic layer and an aqueous layer. The organic layer was collected, while the aqueous layer was twice extracted with 200 mL of toluene. The organic layer and the toluene extracts were combined and analyzed by gas chromatography under the same conditions as in Example 1 to find that the combined organic layer and toluene extracts contains 47.8 g (0.477 mol, yield: 93.1%) of 2-methyl-cis-3-penten-1-ol and 0.82 g (10 mmol, yield: 1.6%) of 2-methyl-trans-3-penten-1-ol (cis/trans=98.3/1.7).

(b) Production of 2-methyl-cis-3-pentenyl acetate

A three-neck flask with a volume of 200 mL was charged with a part of the combined organic layer and toluene extracts obtained in (a) above (containing 8.27 g (83 mmol) of 2-methyl-cis-3-penten-1-ol), 0.512 g (4.2 mmol) of 4-dimethylaminopyridine and 8.8 g (87 mmol) of triethylamine. Then 12.7 g (0.125 mol) of acetic anhydride was added dropwise to the obtained mixture at a rate such that the reaction temperature did not exceed 40° C.

50 mL of diisopropyl ether and 60 mL of 2N-HCl aq. were added to the reaction mixture, followed by stirring. The resulting mixture was allowed to stand and separate into an organic layer and an aqueous layer. The organic layer was collected, washed with 60 ml of 2N-HCl aq. and twice washed with 50 ml of saturated aqueous sodium hydrogen carbonate, successively, and dried over 10 g of sodium sulfate with stirring for 30 minutes. Sodium sulfate was filtered off from the mixture, and the filtrate was analyzed by gas chromatography under the same conditions as in Example 1 to find that the filtrate contains 11.50 g (81 mmol, yield: 98.1%) of 2-methyl-cis-3-pentenyl acetate.

A part of the filtrate obtained above was distilled under reduced pressure to give 2.95 g of 2-methyl-cis-3-pentenyl acetate (boiling point: 62° C./21 Torr, purity: 98.2%) having an apple and floral note. The properties of this compound are shown below.

$^1$H-NMR (300 MHz, CDCl$_3$, TMS)

δ (ppm): 0.99 (d, 3H), 1.64 (q, 3H), 2.05 (s, 3H), 2.80–2.91 (m, 1H), 3.89–3.92 (q, 2H), 5.13–5.21 (m, 1H), 5.46–5.56 (m, 1H)

$^{13}$C-NMR (300 MHz, CDCl$_3$, TMS)

δ (ppm): 13.20, 17.42, 21.11, 31.11, 68.80, 125.41, 132.33, 171.31

Example 3 (Production of 3-methyl-5-phenyl-cis-4-pentenyl acetate)

(a) Production of 3-methyl-5-phenyl-cis-4-penten-1-ol

A Grignard reaction was conducted by the same manner as in Example 1 (a), except that 140 ml of a solution of phenyl magnesium bromide in diethyl ether (concentration: 3.0 mol/liter, containing 0.42 mol of phenyl magnesium bromide) was used instead of the solution of methyl magnesium bromide in diethyl ether, that the amount of 4-methyl-3,4-dihydro-2H-pyran is changed to 39.43 g(0.402 mol) and that the reaction temperature was changed to 50° C.

The reaction mixture was cooled to room temperature, poured into 2 liters of a saturated aqueous ammonium chloride, followed by stirring. Then the mixture was allowed to stand and separate into an organic layer and an aqueous layer. The organic layer was collected, while the aqueous layer was twice extracted with 200 mL of toluene. The organic layer and the toluene extracts were combined and analyzed by gas chromatography under the same conditions as in Example 1 to find that the combined organic layer and toluene extracts contains 70.16 g (0.398 mol, yield: 99%) of 3-methyl-5-phenyl-cis-4-penten-1-ol. However, 3-methyl-5-phenyl-trans-4-penten-1-ol cannot be detected (cis/trans= 100/0).

A part of the combined organic layer and toluene extracts was distilled under reduce pressure to give 36.67 g of 3-methyl-5-phenyl-cis-4-penten-1-ol (boiling point: 101° C./0.9 Torr, Purity: 99.4%) having a camphor-like odor. The properties of this compound are shown below.

$^1$H-NMR (300 MHz, CDCl$_3$, TMS)

δ (ppm): 1.07 (d, 3H), 1.46–1.65 (m, 2H), 2.80–3.00 (m, 1H), 3.50–3.60 (m, 2H), 5.43 (t, 1H), 6.41 (d, 1H), 7.18–7.34 (m, 5H)

$^{13}$C-NMR (300 MHz, CDCl$_3$, TMS)

δ (ppm): 21.33, 29.19, 40.39, 61.27, 126.79, 128.33, 128.42, 128.68, 138.59

(b) Production of 3-methyl-5-phenyl-cis-4-pentenyl acetate

A three-neck flask with a volume of 200 mL was charged with a part of the combined organic layer and toluene extracts obtained in (a) above (containing 27.52 g (0.156 mol) of 3-methyl-5-phenyl-cis-4-penten-1-ol), 0.95 g (7.8 mmol) of 4-dimethylaminopyridine and 23.65 g (0.234 mol) of triethylamine. Then 23.87 g (0.234 mol) of acetic anhydride was added dropwise to the obtained mixture at a rate such that the reaction temperature did not exceed 40° C.

150 mL of n-hexane and 100 mL of 2N-HCl aq. were added to the reaction mixture, followed by stirring. The resulting mixture was allowed to stand and separate into an organic layer and an aqueous layer. The organic layer was collected, washed with 100 ml of 2N-HCl aq. and twice washed with 100 ml of saturated aqueous sodium hydrogen carbonate, successively, and dried over 10 g of sodium sulfate with stirring for 30 minutes. Sodium sulfate was filtered off from the mixture, and the filtrate was analyzed by gas chromatography under the same conditions as in Example 1 to find that the filtrate contains 33.48 g (0.153 mol, yield: 98.3%) of 3-methyl-cis-5-phenyl-4-pentenyl acetate.

The filtrate obtained above was distilled under reduced pressure to give 30.92 g of 3-methyl-5-phenyl-cis-4-pentenyl acetate (boiling point: 89° C./0.3 Torr, purity: 99.3%) having a pear-like and floral note. The properties of this compound are shown below.

$^1$H-NMR (300 MHz, CDCl$_3$, TMS)

δ (ppm): 1.09 (d, 3H), 1.52–1.75 (m, 2H), 1.86 (s, 1H), 2.85–2.98 (m, 1H), 3.94–4.06 (m, 2H), 5.40 (t, 1H), 6.43 (d, 1H), 7.19–7.34 (m, 5H)

$^{13}$C-NMR (300 MHz, CDCl$_3$, TMS)

δ (ppm): 20.94, 21.18, 29.13, 36.10, 62.86, 126.74, 128.32, 128.45, 128.59, 128.72, 128.86, 128.98, 137.73, 171.00

Example 4 (Production of 2-methyl-4-phenyl-cis-3-butenyl acetate)

(a) Production of 2-methyl-4-phenyl-cis-3-buten-1-ol

A Grignard reaction was conducted by the same manner as in Example 1 (a) except that 38.12 g (0.454 mol) of 3-methyl-2,3-dihydrofuran and 150 mL of a solution of phenyl magnesium bromide in diethyl ether (concentration: 3.0 mol/liter, containing 0.45 mol of phenyl magnesium bromide) were used instead of the 4-methyl-3,4-dihydro-2H-pyran and the solution of methyl magnesium bromide in diethyl ether, respectively, and that the reaction temperature was changed to 50° C.

The reaction mixture was cooled to room temperature, poured into 2 liters of a saturated aqueous ammonium chloride, followed by stirring. Then the mixture was allowed to stand and separate into an organic layer and an aqueous layer. The organic layer was collected, while the aqueous layer was twice extracted with 200 mL of toluene. The organic layer and the toluene extracts were combined and analyzed by gas chromatography under the same conditions as in Example 1 to find that the combined organic layer and toluene extracts contains 71.20 g (0.404 mol, yield: 88.9%) of 2-methyl-4-phenyl-cis-3-buten-1-ol. However, 2-methyl-4-phenyl-trans-3-buten-1-ol cannot be detected (cis/trans= 100/0).

A part of the combined organic layer and toluene extracts was distilled under reduced pressure to give 15 g of 2-methyl-4-phenyl-cis-3-buten-1-ol (boiling point: 154° C./2.0 Torr, purity: 99.2%) having a pear-like and floral note. The properties of this compound are shown below.

$^1$H-NMR (300 MHz, CDCl$_3$, TMS)

δ (ppm): 1.02 (d, 3H), 2.97–3.07 (m, 1H), 3.43–3.52 (m, 2H), 5.42 (t, 1H), 6.56 (d, 1H), 7.21–7.33 (m, 5H)

$^{13}$C-NMR (300 MHz, CDCl$_3$, TMS)

δ (ppm): 17.32, 35.40, 67.96, 126.99, 128.22, 128.40, 128.64, 128.77, 130.92, 135.11

(b) Production of 2-methyl-4-phenyl-cis-3-butenyl acetate

A three-neck flask with a volume of 200 mL was charged with a part of the combined organic layer and toluene extracts obtained in (a) above (containing 66.3 g (0.376 mol) of the 2-methyl-4-phenyl-cis-3-buten-1-ol) and 3.90 g (32 mmol) of 4-dimethylaminopyridine and 56.96 g (0.564 mol) of triethylamine. Then 47.94 g (0.470 mol) of acetic anhydride was added dropwise to the obtained mixture at a rate such that the reaction temperature did not exceed 40° C.

30 mL of n-hexane and 50 mL of water were added to the reaction mixture, followed by stirring. The resulting mixture was allowed to stand and separate into an organic layer and an aqueous layer. The organic layer was collected, washed four times with 50 mL of water, and dried over 10 g of sodium sulfate with stirring for 30 minutes. Sodium sulfate was filtered off from the mixture, and the filtrate was analyzed by gas chromatography under the same conditions as in Example 1 to find that the filtrate contains 75.9 g (0.372 mol, yield: 99%) of 2-methyl-4-phenyl-cis-3-butenyl acetate.

The filtrate obtained above was distilled under reduced pressure to give 51.01 g of 2-methyl-4-phenyl-cis-3-butenyl acetate (boiling point: 108° C./2.5 Torr, purity: 99.2%) having a pear-like note. The properties of this compound are shown below.

¹H-NMR (300 MHz, CDCl₃, TMS)

δ (ppm): 1.06 (q, 3H), 2.02 (d, 3H), 3.09–3.19 (m, 1H), 3.92–4.07 (m, 2H), 5.44 (t, 1H), 6.49 (d, 1H), 7.23–7.36 (m, 5H)

¹³C-NMR (300 MHz, CDCl₃, TMS)

δ (ppm): 17.70, 21.08, 32.13, 68.65, 127.0, 128.42, 128.51, 128.68, 128.86, 128.89, 128.94, 130.22, 134.22

Example 5

The components listed in Table 1 were mixed under stirring at room temperature to give fragrance compositions 1 and 2. Table 2 shows the cis-configurational unsaturated esters used in the fragrance compositions.

TABLE 1

(Components of fragrance compositions)

| Component | Parts by weight |
| --- | --- |
| cis-configurational unsaturated ester | 10.0 |
| geraniol | 15.0 |
| citronellol | 30.0 |
| tetrahydrogeraniol | 0.5 |
| nerol | 10.0 |
| linalool | 2.0 |
| phenylethylacohol | 15.0 |
| eugenol | 1.5 |
| citronellyl acetate | 2.0 |
| geranyl acetate | 1.0 |
| phenylethyl acetate | 6.0 |
| dimethyl benzyl acetate | 1.0 |
| ionone | 2.0 |
| γ-methyl ionone | 1.0 |
| citral | 0.5 |
| decanal | 0.3 |
| undecylenaldehyde | 0.2 |
| oil of rose | 2.0 |
| Total | 100.0 |

TABLE 2

| Fragrance Composition | cis-Configurational unsaturated ester used |
| --- | --- |
| 1 | 3-methyl-cis-4-hexenyl acetate |
| 2 | 2-methyl-cis-3-pentenyl acetate |

Example 6 (Production of cis-3-penten-1-ol)

A three-neck flask with a volume of 100 mL was charged with 3.2 mg (0.005 mmol) of dichlorobis(triphenylphosphine) nickel(II), 2.623 g (10 mmol) of triphenylphosphine and 30 mL of toluene under nitrogen. 11.8 mL of a solution of methyl magnesium bromide in diethyl ether (concentration: 2.37 mol/liter, containing 28 mmol of methyl magnesium bromide) was added to the resulting mixture at room temperature, followed by stirring for 15 minutes.

Thereafter, approximately 10 mL of diethyl ether was distilled off from the resulting mixture at a temperature of 25° C. or lower and a pressure of approximately 1 Torr, and 10 mL of toluene was then added to the residue. 1.73 g (24.7 mmol) of 2,3-dihydrofuran was added dropwise to the obtained mixture over 5 minutes at 20° C. under nitrogen. The temperature of the reaction mixture was raised to 50° C., followed by stirring for 5 hours at 50° C. and further stirring for 1 hour at 70° C.

The reaction mixture was cooled to room temperature, and poured into 120 mL of a saturated aqueous ammonium chloride, followed by stirring. Then the mixture was allowed to stand and separate into an organic layer and an aqueous layer. The organic layer was collected, while the aqueous layer was twice extracted with 20 mL of toluene. The organic layer and the toluene extracts were combined and analyzed by gas chromatography under the same analysis conditions as in Example 1 to find that the combined organic layer and toluene extracts contains 2.03 g (23.6 mmol; yield: 95.5%) of cis-3-penten-1-ol. However, trans-3-penten-1-ol cannot be detected (cis/trans=100/0).

Example 7 (Production of cis-4-hexen-1-ol)

A Grignard reaction was carried out by the same manner as in Example 1 (a), except that 37.5 g (0.446 mol) of 3,4-dihydro-2H-pyran was used instead of the 4-methyl-3,4-dihydro-2H-pyran, and that the reaction was conducted at 50° C. for 2 hours.

The reaction mixture was cooled to room temperature, and poured into 2 liters of a saturated aqueous ammonium chloride, followed by stirring. Then the mixture was allowed to stand and separate into an organic layer and an aqueous layer. The organic layer was collected, while the aqueous layer was twice extracted with 200 mL of toluene. The organic layer and the toluene extracts were combined and analyzed by gas chromatography under the same conditions as in Example 1 to find that the combined organic layer and toluene extracts contains 41.39 g (0.413 mol, yield: 94.9%) of cis-4-hexen-1-ol and 0.33 g (3.3 mmol, yield: 0.7%) of trans-4-hexen-1-ol (cis/trans=99.2/0.8).

Example 8 (Production of cis-3-hexen-1-ol)

The procedures of Example 6 was repeated, except that the amounts of the dichlorobis(triphenylphosphine) nickel (II) and the triphenylphosphine were changed to 163.6 mg (0.25 mmol) and 2.625 g (10 mmol), respectively, that 13.9 mL of a solution of ethyl magnesium bromide in diethyl ether (concentration: 2.13 mol/liter, containing 29.6 mmol of ethyl magnesium bromide) was used instead of the solution of methyl magnesium bromide in diethyl ether, and that the stirring of the reaction mixture was carried out for 3 hours at 50° C.

The reaction mixture was cooled to room temperature, and poured into 120 mL of a saturated aqueous ammonium chloride, followed by stirring. Then the mixture was allowed to stand and separate into an organic layer and an aqueous layer. The organic layer was collected, while the aqueous layer was twice extracted with 20 mL of toluene. The organic layer and the toluene extracts were combined and analyzed by gas chromatography under the same conditions as in Example 1 to find that the combined organic layer and toluene extracts contains 0.71 g (7.1 mmol; yield: 29.0%) of cis-3-hexen-1-ol (leaf alcohol) and 0.02 g (0.2 mmol; yield: 0.8%) of trans-3-hexen-1-ol (cis/trans=97.3/2.7).

Reference Example 1 (Production of cis-3-pentenyl acetate)

(a) Production of cis-3-penten-1-ol

A three-neck flask with a volume of 2 liters was charged with 0.548 g (0.835 mmol) of dichlorobis(triphenylphosphine) nickel(II), 0.438 g (1.67 mmol) of triphenylphosphine and 1 liter of mesitylene under nitrogen. 400 mL of a solution of methyl magnesium bromide in diethyl ether (concentration: 2.1 mol/liter, containing 0.84 mol of methyl magnesium bromide) was added to the resulting mixture at room temperature, followed by stirring for 15 minutes.

Thereafter, approximately 210 mL of diethyl ether was distilled off from the resulting mixture at a temperature of 25° C. or lower and a pressure of approximately 1 Torr. 59.06 g (0.843 mol) of 2,3-dihydrofuran was added dropwise to the residue over 10 minutes at 20° C. under nitrogen. The temperature of the reaction mixture was raised to 50° C., followed by stirring for 4 hours at 50° C.

The reaction mixture was cooled to room temperature, and poured into 1.5 liters of a saturated aqueous ammonium chloride, followed by stirring. Then the mixture was allowed to stand and separate into an organic layer and an aqueous layer. The organic layer was collected, while the aqueous layer was extracted with 200 mL of mesitylene. The organic layer and the mesitylene extract were combined and analyzed by gas chromatography under the same conditions as in Example 1 to find that the combined organic layer and mesitylene extract contains 58.96 g (0.69 mol; yield: 81.3%) of cis-3-penten-1-ol. However, trans-3-penten-1-ol cannot be detected (cis/trans=100/0).

(b) Production of cis-3-pentenyl acetate

A three-neck flask with a volume of 200 mL was charged with a part of the combined organic layer and the mesitylene extract obtained in the above (a) (containing 31.92 g (0.371 mol) of cis-3-penten-1-ol) and 2.26 g (18.5 mmol) of 4-dimethylaminopyridine. Then 75.68 g (0.742 mol) of acetic anhydride was added dropwise to the obtained mixture at a rate such that the reaction temperature did not exceed 40° C.

30 mL of n-hexane and 50 mL of water were added to the reaction mixture, followed by stirring. The resulting mixture was allowed to stand and separate into an organic layer and an aqueous layer. The organic layer was collected, twice washed with 50 mL of water, and dried over 10 g of sodium sulfate with stirring for 30 minutes. Sodium sulfate was filtered off from the mixture, and the filtrate was analyzed by gas chromatography under the same conditions as in Example 1 to find that the filtrate contains 43.05 g (0.336 mol; yield: 90.5%) of cis-3-pentenyl acetate.

A part of the filtrate obtained above was purified with column chromatography and distillation under reduced pressure, successively, to give 24.2 g of cis-3-pentenyl acetate (boiling point: 73° C./34 Torr, purity: 99.9%) having a green note with slight floral note.

Reference Example 2 (Production of cis-4-hexenyl acetate)

An acylation with acetic anhydride was carried out by the same manner as in Reference Example 1 (b), except that a part of the combined organic layer and the toluene extracts obtained in Example 7 (containing 38.65 g (0.386 mol) of cis-4-hexen-1-ol) was used instead of the cis-3-penten-1-ol.

100 mL of n-hexane and 50 mL of water were added to the reaction mixture, followed by stirring. The resulting mixture was allowed to stand and separate into an organic layer and an aqueous layer. The organic layer was collected, washed four times with 100 mL of water, and dried over 10 g of sodium sulfate with stirring for 30 minutes. Sodium sulfate was filtered off from the mixture, and the filtrate was analyzed by gas chromatography under the same conditions as in Example 1 to find that the filtrate contains 35.22 g (0.248 mol; yield: 64.2%) of cis-4-hexenyl acetate.

The filtrate obtained above was distilled under reduced pressure to give 26.22 g of cis-4-hexenyl acetate (boiling point: 88° C./33 Torr, purity: 99.0%) having a marine note.

Comparative Example 1 (The case in which the amount of nickel compound is increased, corresponding to the conventional method)

The procedures of Example 6 was repeated, except that the amount of the dichlorobis(triphenylphosphine) nickel(II) was changed to 1.616 g (2.47 mmol, an amount of 10 mol% per one mole of nickel atoms), and that the triphenylphosphine was not used.

The reaction mixture was cooled to room temperature, and poured into 120 mL of a saturated aqueous ammonium chloride, followed by stirring. Then the mixture was allowed to stand and separate into an organic layer and an aqueous layer. The organic layer was collected, while the aqueous layer was twice extracted with 20 mL of toluene. The organic layer and the toluene extracts were combined and analyzed by gas chromatography under the same conditions as in Example 1 to find that the combined organic layer and toluene extracts contains 1.72 g (20.0 mmol; yield: 81.0%) of cis-3-penten-1-ol and 0.30 g (3.5 mmol; yield: 14.0%) of trans-3-penten-1-ol (cis/trans=85.3/14.7).

Obviously, numerous modifications and variations are possible in light of the above teachings. It is therefore to be understood that within the scope of the appended claims the invention may be practiced otherwise than as specifically described therein.

There entire disclosures of the specifications, claims, and summaries of Japanese Patent Applications No. 10-117872 filed on Apr. 13, 1998, and No. 10-345670 filed on Dec. 4, 1998, are hereby incorporated by reference.

What is claimed is:

1. A cis-configurational unsaturated ester represented by the formula:

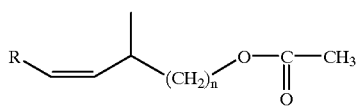

(1)

where R is a methyl group or a phenyl group, and n is 1 or 2.

2. A fragrance composition comprising a cis-configurational unsaturated ester represented by the formula:

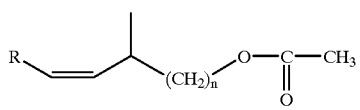

(1)

where R is a methyl group or a phenyl group, and n is 1 or 2, wherein said cis-configurational unsaturated ester has a fruity and green, apple and floral, pear-like and floral or pear-like odor.

3. The fragrance composition of claim 2, wherein the amount of the cis-configurational unsaturated ester of the formula (1) is 0.01% by weight or more of the total weight of the fragrance composition.

4. The fragrance composition of claim 2, wherein the amount of the cis-configurational unsaturated ester of the formula (1) is 0.1 to 95% by weight or more of the total weight of the fragrance composition.

5. The fragrance composition of claim 2, wherein the amount of the cis-configurational unsaturated ester of the formula (1) is 1 to 40% by weight or more of the total weight of the fragrance composition.

6. A process for producing a cis-configurational unsaturated ester represented by the formula:

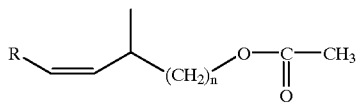 (1)

where R is a methyl group or a phenyl group and n is 1 or 2, comprising the steps of:
reacting a cyclic vinyl ether represented by the formula:

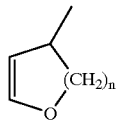 (2a)

where in is defined as above with a Grignard reagent represented by the formula

RMgX (3a)

where R is defined as above, and X is a chlorine atom, a bromine atom or an iodine atom in the presence of a triarylphosphine and not more than 0.05 mol of a nickel compound per one mole of the cyclic vinyl ether represented by the formula (2), to give a cis-configurational unsaturated alcohol represented by the formula:

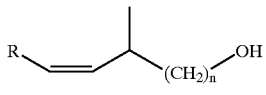 (4a)

where n and R are defined as above; and
subjecting this cis-configurational unsaturated alcohol to acylation wit acetic acid or a derivative thereof to give the cis-configurational unsaturated ester represented by the formula (1).

* * * * *